(12) United States Patent
Flohr et al.

(10) Patent No.: US 7,285,548 B2
(45) Date of Patent: Oct. 23, 2007

(54) UREA SUBSTITUTED BENZOTHIAZOLES

(75) Inventors: Alexander Flohr, Basel (CH); Roland Jakob-Roetne, Inzlingen (DE); Roger David Norcross, Rheinfelden (CH); Claus Riemer, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 429 days.

(21) Appl. No.: 10/854,059

(22) Filed: May 26, 2004

(65) Prior Publication Data

US 2004/0242576 A1    Dec. 2, 2004

(30) Foreign Application Priority Data

May 30, 2003   (EP)   ................... 03012118

(51) Int. Cl.
*A61K 31/5377* (2006.01)
*C07D 413/04* (2006.01)
*C07D 417/04* (2006.01)

(52) U.S. Cl. .................. 514/233.8; 544/106; 544/111; 544/132; 544/135; 514/231.2; 514/231.5; 514/233.5

(58) Field of Classification Search ................ 544/106, 544/111, 132, 133, 135; 514/231.2, 231.5, 514/233.5, 233.8
See application file for complete search history.

(56) References Cited

U.S. PATENT DOCUMENTS 6,521,754 B2 * 2/2003 Alanine et al. ............. 544/129
6,727,247 B2 * 4/2004 Flohr et al. ............... 514/235.2
6,835,732 B2 * 12/2004 Alanine et al. .......... 514/235.5
6,963,000 B2 * 11/2005 Alanine et al. ............. 548/146
7,019,001 B2 * 3/2006 Flohr et al. ............... 514/233.8

FOREIGN PATENT DOCUMENTS

WO    WO 01/97786    12/2001
WO    WO 03/049741 A1    6/2003

* cited by examiner

*Primary Examiner*—Golam M. M. Shameem
(74) *Attorney, Agent, or Firm*—George W. Johnston; Patricia S. Rocha-Tramaloni; Gene J. Yao

(57) ABSTRACT

The present invention relates to compounds of formula I

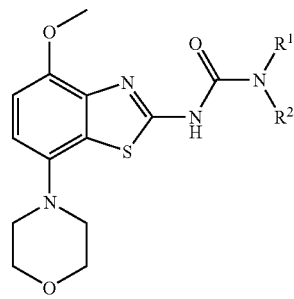

wherein
  $R^1$ and $R^2$ are described herein, and their pharmaceutically acceptable salts thereof for the treatment of diseases, related to the $A_{2A}$ receptor.

10 Claims, No Drawings

UREA SUBSTITUTED BENZOTHIAZOLES

FIELD OF THE INVENTION

The present invention relates to compounds of the general formula

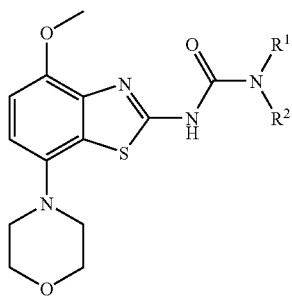

wherein $R^1$, $R^2$ and n are described hereinbelow. These ligands (compounds) have a good affinity to the $A_{2A}$-receptor and a high selectivity to the $A_1$- and $A_3$ receptors. These compounds are useful, inter alia, in treatment of Alzheimer's disease, depression, Parkinson's disease and ADHD.

BACKGROUND OF THE INVENTION

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzym A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtypes has been classically characterized by the adenylate cydase effector system, which utilises cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_s$ proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326-328 amino acids) was cloned from various species (canine, human, rat, dog, chick, bovine, guinea-pig) with 90-95% sequence identify among the mammalian species. The $A_{2A}$ receptor (409-412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317-320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The action of both subtypes is to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neuromodulator, able to modulate many aspects of physiological brain function. Endogenous adenosine, a central link between energy metabolism and neuronal activity, varies according to behavioral state and (patho) physiological conditions. Under conditions of increased demand and decreased availability of energy (such as hypoxia, hypoglycemia, and/or excessive neuronal activity), adenosine provides a powerful protective feedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents.

Adenosine antagonists stimulate the activity of the CNS and have proven to be effective as cognition enhancers. Selective $A_{2a}$ antagonists have therapeutic potential in the treatment of various forms of dementia, for example in Alzheimer's disease, and of neurodegenerative disorders, e.g. stroke. Adenosine $A_{2a}$ receptor antagonists modulate the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, cannabinoids). Drugs acting at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyper-activity disorder).

An important role for adenosine in the cardiovascular system is as a cardioprotective agent. Levels of endogenous adenosine increase in response to ischaemia and hypoxia, and protect cardiac tissue during and after trauma (preconditioning). By acting at the $A_1$ receptor, adenosine $A_1$ agonists may protect against the injury caused by myocardial ischemia and reperfusion. The modulating influence of $A_{2}a$ receptors on adrenergic function may have implications for a variety of disorders such as coronary artery disease and heart failure. $A_{2a}$ antagonists may be of therapeutic benefit in situations in which an enhanced antiadrenergic response is desirable, such as during acute myocardial ischemia. Selective antagonists at $A_{2a}$ receptors may also enhance the effectiveness of adenosine in terminating supraventricula arrhytmias.

Adenosine modulates many aspects of renal function, including renin release, glomerular filtration rate and renal blood flow. Compounds which antagonise the renal affects of adenosine have potential as renal protective agents. Furthermore, adenosine $A_3$ and/or $A_{2B}$ antagonists may be useful in the treatment of asthma and other allergic responses or and in the treatment of diabetes mellitus and obesity.

Numerous documents describe the current knowledge on adenosine receptors. These include Bioorganic & Medicinal Chemistry, 6, (1998), 619-641; Bioorganic & Medicinal Chemistry, 6, (1998), 707-719; J. Med. Chem., (1998), 41, 2835-2845; J. Med. Chem., (1998), 41, 3186-3201; J. Med. Chem., (1998), 41, 2126-2133; J. Med. Chem., (1999), 42, 706-721; J. Med. Chem., (1996), 39, 1164-1171; Arch. Pharm. Med. Chem., 332, 39-41, (1999); Am. J. Physiol., 276, H1113-1116, (1999) and Naunyn Schmied, Arch. Pharmacol. 362, 375-381, (2000).

SUMMARY OF THE INVENTION

An aspect of the present invention is directed to a compound of formula I

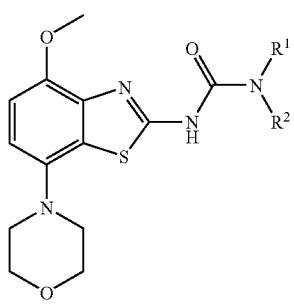

I wherein
$R^1$ is selected from the group consisting of
cyclopentyl,
cyclopentyl substituted by $CF_3$,
cyclopentyl substituted by lower alkyl,
cyclopentyl substituted by —$(CH_2)_n$OH,
cyclopentyl substituted by —$(CH_2)_n$—O-lower alkyl,
cyclohexyl,
cyclohexyl substituted by $CF_3$,
cyclohexyl substituted by lower alkyl,
cyclohexyl substituted by —$(CH_2)_n$OH,
cyclohexyl substituted by —$(CH_2)_n$—O-lower alkyl,
1-bicyclo[2.2.1]hept-2-yl,
1-(7-oxa-bicyclo[2.2.1]hept-2-yl,
1-(5-exo-hydroxy-bicyclo[2.2.1]hept-2-exo-yl,
1-(5-exo-hydroxy-bicyclo[2.2.1]hept-2-endo-yl, and
1-adamantan-1-yl; and
$R^2$ is lower alkyl; or
$R^1$ and $R^2$ form together with the N-atom the group
8-oxa-3-aza-bicyclo[3.2.1]octane; and
n is 0 or 1;
or a pharmaceutically acceptable salt thereof.

Other embodiments of this invention are directed to methods of manufacturing compounds of formula I, a pharmaceutical composition containing a compound of formula I, and a pharmaceutically acceptable salt thereof, as well as a method of controlling or prevention of illnesses based on the modulation of the adenosine system, such as Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse comprising administering to a patient a therapeutically effective amount of a compound of formula I or a pharmaceutically acceptable salt thereof.

Furthermore, compounds of the present invention are useful as sedatives, muscle relaxants, antipsychotics, antiepileptics, anticonvulsants and cardiaprotective agents for disorders such as coronary artery disease and heart failure. Preferred indications in accordance with the present invention are those that depend on the $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DETAILED DESCRIPTION OF THE INVENTION

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "therapeutically effective amount" refers to an amount of at least one compound of formula I, or a pharmaceutically acceptable salt thereof, tha modulates adenosine.

The present invention is related to a compound of formula I

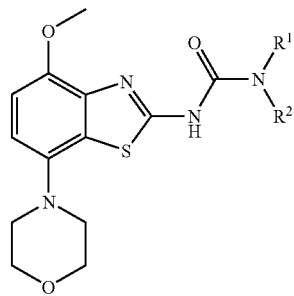

I wherein
R¹ is selected from the group consisting of
cyclopentyl,
cyclopentyl substituted by CF₃,
cyclopentyl substituted by lower alkyl,
cyclopentyl substituted by —(CH₂)$_n$OH,
cyclopentyl substituted by —(CH₂)$_n$—O-lower alkyl,
cyclohexyl,
cyclohexyl substituted by CF₃,
cyclohexyl substituted by lower alkyl,
cyclohexyl substituted by —(CH₂)$_n$OH,
cyclohexyl substituted by —(CH₂)$_n$—O-lower alkyl,
1-bicyclo[2.2.1]hept-2-yl,
1-(7-oxa-bicyclo[2.2.1]hept-2-yl,
1-(5-exo-hydroxy-bicyclo [2.2.1]hept-2-exo-yl,
1-(5-exo-hydroxy-bicyclo [2.2.1]hept-2-endo-yl, and
1-adamantan-1-yl; and
R² is lower alkyl; or
R¹ and R² form together with the N-atom the group 8-oxa-3-aza-bicyclo[3.2.1]octane; and
n is 0 or 1;
or a pharmaceutically acceptable salt thereof.

In another embodiment, the present invention is related to a compound of formula I

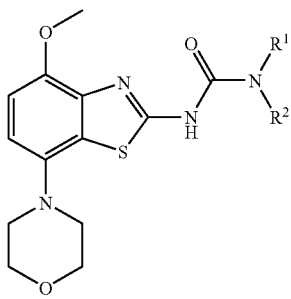

I wherein
R¹ is selected from the group consisting of
cyclopentyl,
cyclopentyl substituted by CF₃,
cyclopentyl substituted by lower alkyl,
cyclopentyl substituted by —(CH₂)$_n$OH,
cyclopentyl substituted by —(CH₂)$_n$—O-lower alkyl,
cyclohexyl,
cyclohexyl substituted by CF₃,
cyclohexyl substituted by lower alkyl,
cyclohexyl substituted by —(CH₂)$_n$OH,
cyclohexyl substituted by —(CH₂)$_n$—O-lower alkyl,
1-bicyclo[2.2.1]hept-2-yl,
1-(7-oxa-bicyclo[2.2.1]hept-2-yl,
1-(5-exo-hydroxy-bicyclo[2.2.1]hept-2-exo-yl,
1-(5-exo-hydroxy-bicyclo[2.2.1]hept-2-endo-yl, and
1-adamantan-1-yl;
R² is lower alkyl; and
n is 0 or 1;
or a pharmaceutically acceptable salt thereof.

In another embodiment, this invention is related to a compound of formula I

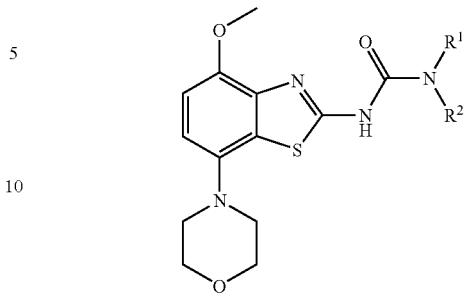

I wherein, R¹ and R² form together with the N-atom the group 8-oxa-3-aza-bicyclo[3.2.1]octane;
or a pharmaceutically acceptable salt thereof.

In a preferred embodiment, the compound of formula I is where R¹ is cyclopentyl.

In another preferred embodiment, the compound of formula I is where R¹ is cyclopentyl substituted by CF₃.

In another preferred embodiment, the compound of formula I is where R¹ is cyclopentyl substituted by lower alkyl.

In another preferred embodiment, the compound of formula I is where R¹ is cyclopentyl substituted by —(CH₂)$_n$OH, and n is 0 or 1.

In another preferred embodiment, the compound of formula I is where R¹ is cyclopentyl substituted by —(CH₂)$_n$—O-lower alkyl, and n is 0 or 1.

In another preferred embodiment, the compound of formula I is where R¹ is cyclohexyl.

In another preferred embodiment, the compound of formula I where R¹ is cyclohexyl substituted by CF₃.

In another preferred embodiment, the compound of formula I is where R¹ iscyclohexyl substituted by lower alkyl.

In another preferred embodiment, the compound of formula I is where R¹ is cyclohexyl substituted by —(CH₂)$_n$OH, and n is 0 or 1.

In another preferred embodiment, the compound of formula I is where R¹ is cyclohexyl substituted by —(CH₂)$_n$—O-lower alkyl, and n is 0 and 1.

In another preferred embodiment, the compound of formula I is where R¹ is 1-bicyclo[2.2.1]hept-2-yl.

In another preferred embodiment, the compound of formula I is where R¹ is 1-(7-oxa-bicyclo[2.2.1]hept-2-yl.

In another preferred embodiment, the compound of formula I is where R¹ is 1-(5-exo-hydroxy-bicyclo[2.2.1]hept-2-exo-yl.

In another preferred embodiment, the compound of formula I is where R¹ is 1-(5-exo-hydroxy-bicyclo[2.2.1]hept-2-endo-yl.

In another preferred embodiment, the compound of formula I is where R¹ is 1-adamantan-1-yl.

In another preferred embodiment, the compound of formula I is where R¹ and R² form together with the N-atom the group 8-oxa-3-aza-bicyclo[3.2.1]octane.

Preferred compounds are those, wherein R¹ is cyclopentyl, cyclopentyl substituted by CF₃, cyclopentyl substituted by lower alkyl, cyclopentyl substituted by —(CH₂)$_n$OH, cyclopentyl substituted by —(CH₂)$_n$—O-lower alkyl, cyclohexyl, cyclohexyl substituted by CF₃, cyclohexyl substituted by lower alkyl, cyclohexyl substituted by —(CH₂)$_n$OH, cyclohexyl substituted by —(CH₂)$_n$—O-lower alkyl, for example the following compounds:

3-(4-methoxy-7-morpholin-4-yl-benzothiazol-2-yl)-1-methyl-1-(4-trifluoromethyl-cyclohexyl)-urea,
(trans)-3-(4-methoxy-7-morpholin-4-yl-benzothiazol-2-yl)-1-methyl-1-(4-methyl-cyclohexyl urea,
(trans)-1-(4-hydroxymethyl-cyclohexyl)-3-(4-methoxy-7-morpholin-4-yl-benzothiazol-2-yl)-1-methyl-urea,
(trans)-1-(4-methoxymethyl-cyclohexyl)-3-(4-methoxy-7-morpholin-4-yl-benzothiazol-2-yl)-1-methyl-urea or
(rac), (cis-1-(3-hydroxymethyl-cyclopentyl)-3-(4-methoxy-7-morpholin-4-yl-benzothiazol-2-yl)-1-methyl-urea.

Further preferred are those compounds, wherein $R^1$ is
1-bicyclo[2.2.1]hept-2-yl, 1-(7-oxa-bicyclo[2.2.1]hept-2-yl, 1-(5-exo-hydroxy-bicyclo[2.2.1]hept-2-exo-yl, 1-(5-exo-hydroxy-bicyclo[2.2.1]hept-2-endo-yl or
1-adamantan-1-yl, for example the following compounds:
1-(endo)-(rac)-bicyclo[2.2.1]hept-2-yl-3-(4-methoxy-7-morpholin-4-yl-benzothiazol-2-yl)-1-methyl-urea,
(exo)-(+)-3-(4-methoxy-7-morpholin-4-yl-benzothiazol-2-yl)-1-methyl-1-(7-oxa-bicyclo[2.2.1]hept-2-yl)-urea,
(exo)-(−)-3-(4-methoxy-7-morpholin-4-yl-benzothiazol-2-yl)-1-methyl-1-(7-oxa-bicyclo[2.2.1]hept-2-yl)-urea,
(rac)-(endo)-3-(4-methoxy-7-morpholin-4-yl-benzothiazol-2-yl)-1-methyl-1-(7-oxa-bicyclo[2.2.1]hept-2-yl)-urea,
(rac)-1-(5-exo-hydroxy-bicyclo[2.2.1]hept-2-exo-yl)-3-(4-methoxy-7-morpholin-4-yl-benzothiazol-2-yl)-1-methyl-urea,
(rac)-1-(5-exo-hydroxy-bicyclo[2.2.1]hept-2-endo-yl)-3-(4-methoxy-7-morpholin-4-yl-benzothiazol-2-yl)-1-methyl-urea or
1-adamantan-1-yl-3-(4-methoxy-7-morpholin-4-yl-benzothiazol-2-yl)-1-methyl-urea.

An example for compounds, wherein $R^1$ and $R^2$ form together with the N-atom the group 8-oxa-3-aza-bicyclo[3.2.1]octane is 8-oxa-3-aza-bicyclo [3.2.1]octane-3-carboxy acid (4-methoxy-7-morpholin-4-yl-benzothiazol-2-yl)-amide.

The present compounds of formula I and their pharmaceutically acceptable salts can be prepared by methods known in the art, for example, by processes described below, which process comprises reacting a compound of formula to produce a compound of formula

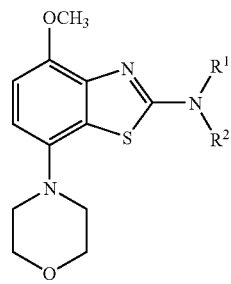

I wherein $R^1$ is selected from the group consisting of
cyclopentyl,
cyclopentyl substituted by $CF_3$,
cyclopentyl substituted by lower alkyl,
cyclopentyl substituted by —$(CH_2)_n$OH,
cyclopentyl substituted by —$(CH_2)_n$—O-lower alkyl,
cyclohexyl,
cyclohexyl substituted by $CF_3$,
cyclohexyl substituted by lower alkyl,
cyclohexyl substituted by —$(CH_2)_n$OH,
cyclohexyl substituted by —$(CH_2)_n$—O-lower alkyl,
1-bicyclo[2.2.1]hept-2-yl,
1-(7-oxa-bicyclo[2.2.1]hept-2-yl,
1-(5-exo-hydroxy-bicyclo[2.2.1]hept-2-exo-yl,
1-(5-exo-hydroxy-bicyclo[2.2.1]hept-2-endo-yl, and
1-adamantan-1-yl; and
$R^2$ is lower alkyl; and
n is 0 or 1.

The present compounds of formula I and their pharmaceutically acceptable salts can also be prepared by methods known in the art, for example, by processes described below, which process comprises reacting a compound of formula

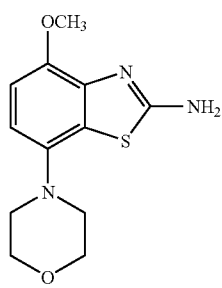

II with a compound of formula

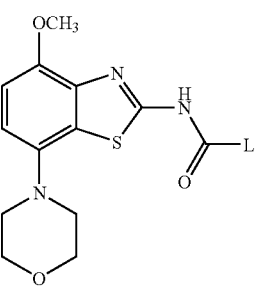

IV with a compound of formula

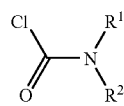

III

V to produce a compound of formula

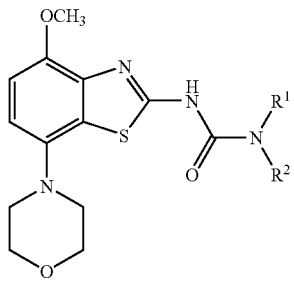

wherein R¹ is selected from the group consisting of
cyclopentyl,
cyclopentyl substituted by $CF_3$,
cyclopentyl substituted by lower alkyl,
cyclopentyl substituted by —$(CH_2)_n$OH,
cyclopentyl substituted by —$(CH_2)_n$—O-lower alkyl,
cyclohexyl,
cyclohexyl substituted by $CF_3$,
cyclohexyl substituted by lower alkyl,
cyclohexyl substituted by —$(CH_2)_n$OH,
cyclohexyl substituted by —$(CH_2)_n$—O-lower alkyl,
1-bicyclo[2.2.1]hept-2-yl,
1-(7-oxa-bicyclo[2.2.1]hept-2-yl,
1-(5-exo-hydroxy-bicyclo[2.2.1]hept-2-exo-yl,
1-(5-exo-hydroxy-bicyclo[2.2.1]hept-2-endo-yl, and
1-adamantan-1-yl; and R² is lower alkyl;
n is 0 or 1;
L is a leaving group selected from the group consisting of halogen, —O-phenyl and O-lower alkyl.

If desired, the resulting compound in the above two processes can further be converted into its pharmaceutically acceptable salt.

In Examples 1-13 and in the following schemes 1 and 2 the preparation of compounds of formula I are described in more detail.

The starting materials are known compounds or may be prepared according to methods known in the art.

Preparation of Compounds of Formula I

The intermediate 7-(morpholin-4-yl)-4-methoxy-benzothiazol-2-ylamine (II) may be prepared according to methods disclosed in WO01/97786. The preparation of compounds of formula (I) using the intermediate of formula (II) is also described in WO01/97786.

One method of preparation-of compounds of formula (I) in accordance with the following scheme 1 is as follows: To a solution of the compound of formula (II) in dichloromethane is subsequently added a base, e.g. pyridine or diisopropyl-ethylamine and a compound of formula (III), and the resulting solution is stirred for about 45 min at ambient temperature. Saturated aqueous sodium hydrogen carbonate is added, the organic phase is separated and dried.

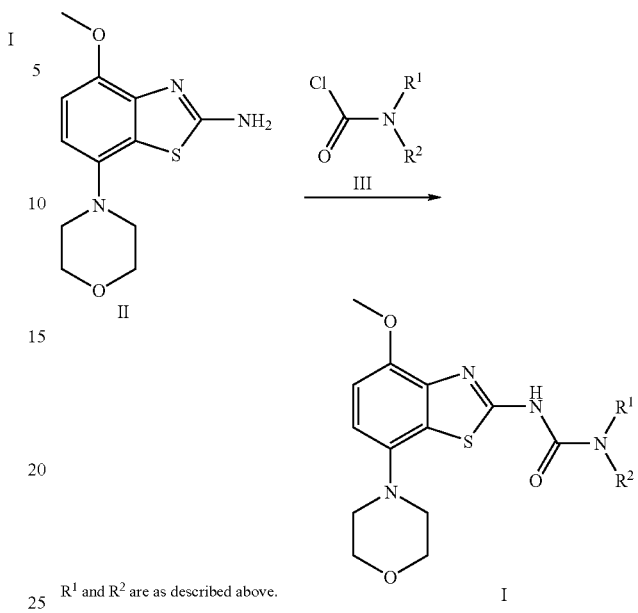

Scheme 1

R¹ and R² are as described above.

Another method of preparation of compounds of formula (I) is as follows: To a solution of the compound of formula (IV), which can be prepared according to methods well known to the art and which is described in WO01/97786, in an inert solvent, e.g. dichloromethane, is subsequently added a base, e.g. pyridine or diisopropyl-ethylamine and a compound of formula (V), and the resulting solution is stirred for about 45 min at 45° C. After cooling to ambient temperature, saturated aqueous sodium hydrogen carbonate is added, the organic phase is separated and dried.

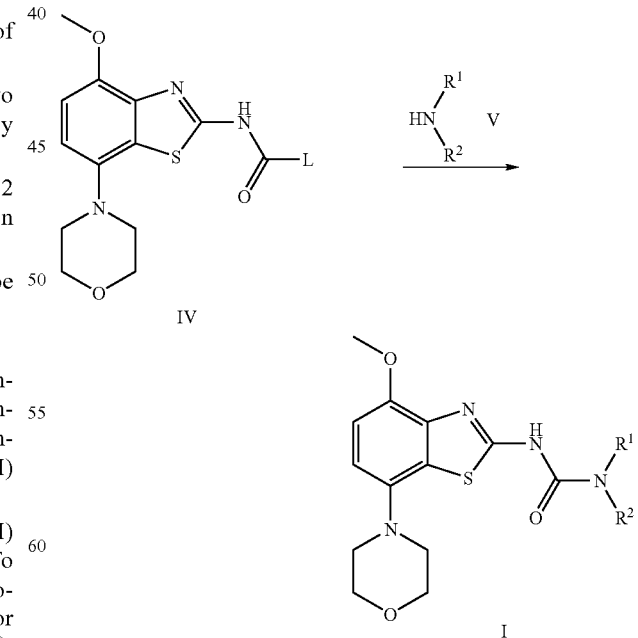

Scheme 2

R¹ and R² are as described above, L is a leaving group such as halogen, —O-phenyl or O-lower alkyl.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used.

Salts of Compounds of Formula I

The compounds of formula I maybe basic, for example in cases where the residue R contains a basic group such as an aliphatic or aromatic amine moiety. In such cases the compounds of formula I may be converted to a corresponding salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic add, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically acceptable salts possess valuable pharmacological properties. Specifically, it has been found that the compounds of the present invention are adenosine receptor ligands and possess a high affinity towards the adenosine $A_{2A}$ receptor.

The compounds were investigated in accordance with the test given hereinafter.

Human Adenosine $A_{2A}$ Receptor

The human adenosine $A_{2A}$ receptor was recombinantly expressed in Chinese hamster ovary (CHO) cells using the semliki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-SCH-58261 (Dionisotti et al., 1997, Br J Pharmacol 121, 353; 1nM) binding assay was carried out in 96-well plates in the presence of 2.5 μg of membrane protein, 0.5 mg of Ysi-poly-l-lysine SPA beads and 0.1 U adenosine deaminase in a final volume of 200 μl of buffer A. Non-specific binding was defined using xanthine amine congener (XAC; 2 μM). Compounds were tested at 10 concentrations from 10 μM-0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

The pKi value of compounds of the present application are in the range of 7.3 to 8.5, as described in the table below.

| Example No. | $hA_2$ (pKi) | Example No. | $hA_2$ (pKi) |
| --- | --- | --- | --- |
| 1 | 7.7 | 8 | 8.0 |
| 2 | 7.8 | 9 | 7.9 |
| 3 | 7.8 | 10 | 8.1 |
| 4 | 7.7 | 11 | 8.1 |
| 5 | 8.4 | 12 | 7.3 |
| 6 | 8.1 | 13 | 8.0 |
| 7 | 8.5 | | |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of soppositories, parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

The most preferred indications in accordance with the present invention are those, which include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| Item | Ingredients | 5 mg | 25 mg | 100 mg | 500 mg |
|---|---|---|---|---|---|
| | | | | mg/tablet | |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredients | 5 mg | 25 mg | 100 mg | 500 mg |
|---|---|---|---|---|---|
| | | | | mg/capsule | |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The following preparation and examples illustrate the invention but are not intended to limit its scope.

EXAMPLE 1

3-(4-Methoxy-7-morpholin-4-yl-benzothiazol-2-yl)-1-methyl-1-(4-trifluoromethyl-cyclohexyl)-urea 4-Methoxy-7-morpholin-4-yl-benzothiazol-2-ylamine was first reacted with phenyl chloroformate as described for (4-methoxy-7-phenyl-benzothiazol-2-yl)-carbamic acid benzyl ester in WO01/97786 and then with methyl-(4-trifluoromethyl-cyclohexyl)-amine. Usual workup, flash-chromatography (silica, eluent dichloromethane/methanol) and final evaporation of the solvent afforded the title compound as white crystals (96% yield), mp 157-167° C. MS: m/e=473(M+H$^+$). Following the general method of example 1 the compounds of examples 2 to 12 were prepared.

EXAMPLE 2

(trans)-3-(4-Methoxy-7-morpholin-4-yl-benzothiazol-2-yl)-1-methyl-1-(4-methyl-cyclohexyl)-urea Using 4-methoxy-7-morpholin-4-yl-benzothiazol-2-ylamine, phenyl chloroformate and (trans)-methyl-(4-methyl-cyclohexyl)-amine, the title compound was prepared as off-white crystals (70% yield), mp 171-173° C. MS: m/e=420(M+H$^+$).

EXAMPLE 3

(trans)-1-(4-Hydroxymethyl-cyclohexyl)-3-(4-methoxy-7-morpholin-4-yl-benzothiazol-2-yl)-1-methyl-urea Using 4-methoxy-7-morpholin-4-yl-benzothiazol-2-ylamine, phenyl chloroformate and (trans)-(4-hydroxymethyl-cyclohexyl)-methyl-amine, the title compound was prepared as light brown crystals (42% yield). MS: m/e=436 (M+H$^+$), mp 190° C. (dec).

EXAMPLE 4

(trans)-1-(4-Methoxymethyl-cyclohexyl)-3-(4-methoxy-7-morpholin-4-yl-benzothiazol-2-yl)-1-methyl-urea Using 4-methoxy-7-morpholin-4-yl-benzothiazol-2-ylamine, phenyl chloroformate and (trans)-(4-methoxymethyl-cyclohexyl)-methyl-amine, the title compound was prepared as white solid (73% yield), mp 141-143° C. MS: m/e=450(M+H$^+$).

EXAMPLE 5

(rac),(cis)-1-(3-Hydroxymethyl-cyclopentyl)-3-(4-methoxy-7-morpholin-4-yl-benzothiazol-2-yl)-1-methyl-urea Using 4-methoxy-7-morpholin-4-yl-benzothiazol-2-ylamine, phenyl chloroformate and (rac)-(cis)-(3-methylamino-cyclopentyl)-methanol, the title compound was prepared as light yellow solid (58% yield), mp 115-118° C. MS: m/e=421 (M+H$^+$).

EXAMPLE 6

1-(endo)-(rac)-Bicyclo[2.2.1]hept-2-yl-3-(4-methoxy-7-morpholin-4-yl-benzothiazol-2-yl)-1-methyl-urea Using 4-methoxy-7-morpholin-4-yl-benzothiazol-2-ylamine, phenyl chloroformate and (endo)-(rac)-(bicyclo[2.2.1]hept-2-yl)-methyl-amine, the title compound was prepared as white solid (65% yield), mp 199-202° C. MS: m/e=417(M+H$^+$).

EXAMPLE 7

(exo)-(+)-3-(4-Methoxy-7-morpholin-4-yl-benzothiazol-2-yl)-1-methyl-1-(7-oxa-bicyclo[2.2.1]hept-2-yl)-urea Using 4-methoxy-7-morpholin-4-yl-benzothiazol-2-ylamine, phenyl chloroformate and (−)-(exo)-methyl-(7-oxa-bicyclo[2.2.1]hept-2-yl)-amine, the title compound was prepared as light yellow crystals (82% yield), mp 202-204° C. MS: m/e=419(M+H$^+$).

EXAMPLE 8

(exo)-(−)-3-(4-Methoxy-7-morpholin-4-yl-benzothiazol-2-yl)-1-methyl-1-(7-oxa-bicyclo[2.2.1]hept-2-yl)-urea Using 4-methoxy-7-morpholin-4-yl-benzothiazol-2-ylamine, phenyl chloroformate and (+)-(exo)-methyl-(7-oxa-bicyclo[2.2.1]hept-2-yl)-amine, the title compound was prepared as light yellow crystals (82% yield), mp 202-203° C. MS: m/e=419(M+H$^+$).

EXAMPLE 9

(rac)-(endo)-3-(4-Methoxy-7-morpholin-4-yl-benzothiazol-2-yl)-1-methyl-1-(7-oxa-bicyclo[2.2.1]hept-2-yl)-urea Using 4-methoxy-7-morpholin-4-yl-benzothiazol-2-ylamine, phenyl chloroformate and (rac)-(endo)-methyl-(7-oxa-bicyclo[2.2.1]hept-2-yl)-amine, the title compound was prepared as white crystals (47% yield), mp 191-193° C. MS: m/e=419(M+H$^+$).

EXAMPLE 10

(rac)-1-(5-exo-Hydroxy-bicyclo[2.2.1]hept-2-exo-yl)-3-(4-methoxy-7-morpholin-4-yl-benzothiazol-2-yl)-1-methyl-urea Using 4-methoxy-7-morpholin-4-yl-benzothiazol-2-ylamine, phenyl chloroformate and 5-(exo)-methylamino-bicyclo[2.2.1]heptan-2-(exo)-ol, the title compound was prepared as white crystals (10% yield), MS: m/e=433(M+H$^+$), mp 189° C.

EXAMPLE 11

(rac)-1-(5-exo-Hydroxy-bicyclo[2.2.1]hept-2-endo-yl)-3-(4-methoxy-7-morpholin-4-yl-benzothiazol-2-yl)-1-methyl-urea Using 4-methoxy-7-morpholin-4-yl-benzothiazol-2-ylamine, phenyl chloroformate and 5-(endo)-methylamino-bicyclo[2.2.1]heptan-2-(exo)-ol, the title compound was prepared as white crystals (12% yield), MS: m/e=433(M+H$^+$), mp 189° C.

EXAMPLE 12

1-Adamantan-1-yl-3-(4-methoxy-7-morpholin-4-yl-benzothiazol-2-yl)-1-methyl-urea

Using 4-methoxy-7-morpholin-4-yl-benzothiazol-2-ylamine, phenyl chloroformate and adamantan-1-yl-methyl-amine, the title compound was prepared as white crystals (76% yield), mp 165-176° C. MS: m/e=458(M+H$^+$).

EXAMPLE 13

8-Oxa-3-aza-bicyclo[3.2.1]octane-3-carboxylic acid (4-methoxy-7-morpholin-4-yl-benzothiazol-2-yl)-amide Using 4-methoxy-7-morpholin-4-yl-benzothiazol-2-ylamine, phenyl chloroformate and 8-oxa-3-aza-bicyclo[3.2.1]octane, the title compound was prepared as white crystals (67% yield), mp 229-231° C. MS: m/e=405(M+H$^+$).

Intermediates

EXAMPLE 14

Methyl-(4-trifluoromethyl-cyclohexyl)-amine

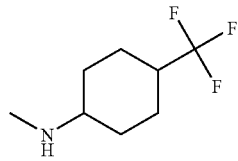

The title compound was prepared from 4-trifluoromethyl-cyclohexylamine (DE 2630562) by introduction of a ethoxycarbonyl-group under standard conditions (ethyl chloroformate/diisopropyl-ethalamine), and final reduction with lithium aluminium hydride in tetrahydrofurane under standard conditions to give the title compound as a light yellow oil, MS: m/e=168(M+H$^+$). The title compound was crystallized as its hydrochloride by use of ethanolic hydrogen chloride. White crystals, mp 202-204° C.

EXAMPLE 15

1-Methyl-4-(ds)-methylamino-cyclohexanol

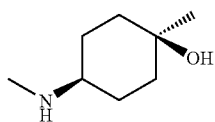

The title compound was prepared from (cis)-4-amino-1-methyl-cyclohexanol (WO9607657) in the same manner as described for methyl-(4-trifluoromethyl-cyclohexyl)-amine. White crystals, mp 123-124° C., MS: m/e=144(M+H$^+$).

EXAMPLE 16

(−)-(exo)-Methyl-(7-oxa-bicyclo[2.2.1]hept-2-yl)-amine hydrochloride

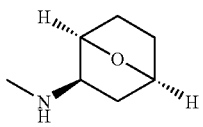

The title compound was prepared from (rac)-(exo)-methyl-(7-oxa-bicyclo[2.2.1]hept-2-yl)-amine (J. Med. Chem. 1971, 14, 698) by benzylation under standard conditions (benzyl bromide/diisopropyl-ethalamine), chiral resolution by preparative chiral HPLC (Chrialpak AD, eluent 2% isopropanol in heptane) and final deprotection under standard conditions (chloroethyl chloroformate/methanol) to give the title compound as white solid. $[\alpha]_D = -6.2$ (c=0.23, dichloromethane).

The anantiomer (+)-(exo)-methyl-(7-oxa-bicyclo[2.2.1]hept-2-yl)-amine hydrochloride was obtained from the earlier eluting fractions of the same resolution.

The invention claimed is:

1. A compound of formula I

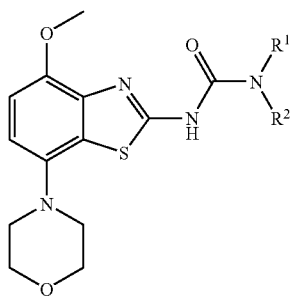

I wherein
$R^1$ is selected from the group consisting of
  cyclopentyl,
  cyolopentyl substituted by $CF_3$,
  cyclopentyl substituted by lower alkyl,
  cyclopentyl substituted by —$(CH_2)_n$OH,
  cyclopentyl substituted by —$(CH_2)_n$—O-lower alkyl,
  cyclohexyl,
  cyclohexyl substituted by $CF_3$,
  cyclohexyl substituted by lower alkyl,
  cyclohexyl substituted by —$(CH_2)_n$OH,
  cyclohexyl substituted by —$(CH_2)_n$—O-lower alkyl,
  1-bicyclo[2.2.1]hept-2-yl,
  1-(7-oxa-bicyclo[2.2.1]hept-2-yl,
  1-(5-exo-hydroxy-bicyclo[2.2.1]hept-2-exo-yl,
  1-(5-exo-hydroxy-bicyclo[2.2.1]hept-2-endo-yl, and
  1-adamantan-1-yl; and
$R^2$ is lower alkyl; and
n is 0 or 1;
or a pharmaceutically acceptable salt thereof.

2. The compound of formula I in accordance with claim 1, wherein $R^1$ is selected from the group consisting of
  cyclopentyl,
  cyclopentyl substituted by $CF_3$,
  cyolopentyl substituted by lower alkyl,
  cyclopentyl substituted by —$(CH_2)_n$OH,
  cyclopentyl substituted by —$(CH_2)_n$—O-lower alkyl,
  cyclohexyl,
  cyclohexyl substituted by $CF_3$,
  cyclohexyl substituted by lower alkyl,
  cyclohexyl substituted by —$(CH_2)_n$OH, and
  cyclohexyl substituted by —$(CH_2)_n$—O-lower alkyl.

3. The compound of formula I in accordance with claim 2, selected from the group consisting of
  3-(4-methoxy-7-morpholin-4-yl-benzothiazol-2-yl)-1-methyl-1-(4-trifluoromethyl-cyclohexyl)-urea,
  (trans)-3-(4-methoxy-7-morpholin-4-yl-benzothiazol-2-yl)-1-methyl-1-(4-methyl-cyclohexyl)-urea,
  (trans)-1-(4-hydroxymethyl-cyclohexyl)-3-(4-methoxy-7-morpholin-4-yl-benzothiazol-2-yl)-1-methyl-urea,
  (trans)-1-(4-methoxymethyl-cyclohexyl)-3-(4-methoxy-7-morpholin-4-yl-benzothiazol-2-yl)-1 -methyl-urea, and
  (rac),(cis)-1-(3-hydroxymethyl-cyolopentyl)-3-(4-methoxy-7-morpholin-4-yl-benzothiazol-2-yl)-1-methyl-urea.

4. The compound of formula I in accordance with claim 1, wherein $R^1$ is selected from the group consisting of
  1-bicyclo[2.2.1]hept-2-yl, 1-(7-oxa-bicyclo[2.2.1]hept-2-yl,
  1-(5-exo-hydroxy-bicyclo[2.2.1]hept-2-exo-yl, and
  1-(5-exo-hydroxy-bicyclo[2.2.1]hept-2-endo-yl or 1-adamantan-1-yl.

5. The compound of formula I in accordance with claim 4, selected from the group consisting of
  1-(endo)-(rac)-bicyclo[2.2.1]hept-2-yl-3-(4-methoxy-7-morpholin-4-yl-benzothiazol-2-yl)-1-methyl-urea,
  (exo)-(+)-3-(4-methoxy-7-morpholin-4-yl-benzothiazol-2-yl)-1-methyl-1-(7-oxa-bicyclo[2.2.1]hept-2-yl)-urea,
  (exo)-(−)-3-(4-methoxy-7-morpholin-4-yl-benzothiazol-2-yl)-1-methyl-1-(7-oxa-bicyclo[2.2.1]hept-2-yl)-urea,
  (rac)-(endo)-3-(4-methoxy-7-morpholin-4-yl-benzothiazol-2-yl)-1-methyl-1-(7-oxa-bicyclo[2.2.1]hept-2-yl)-urea,
  (rac)-1-(5-exo-hydroxy-bicyclo[2.2.1]hept-2-exo-yl)-3-(4-methoxy-7-morpholin-4-yl-benzothiazol-2-yl)-1-methyl-urea,
  (rac)-1-(5-exo-hydroxy-bicyclo[2.2.1]hept-2-endo-yl)-3-(4-methoxy-7-morpholin-4-yl-benzothiazol-2-yl)-1-methyl-urea, and
  1-adamantan-1-yl-3-(4-methoxy-7-morpholin-4-yl-benzothiazol-2-yl)-1-methyl-urea.

6. A process for preparing a compound of formula I as defined in claim 1, which process comprises reacting a compound of formula

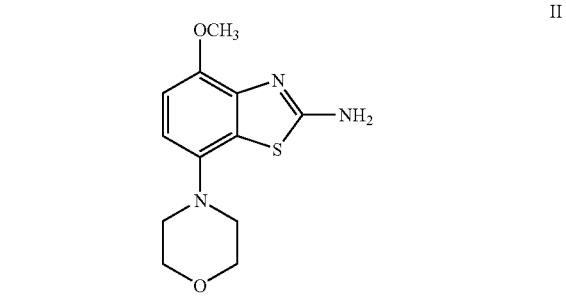

II with a compound of formula

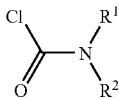

III to produce a compound of formula

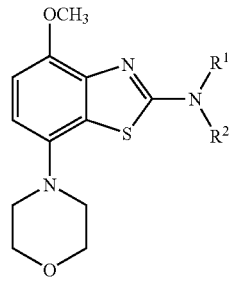

I wherein R¹ is selected from the group consisting of
cyclopentyl,
cyclopentyl substituted by $CF_3$,
cyclopentyl substituted by lower alkyl,
cyolopentyl substituted by —$(CH_2)_n$OH,
cyclopentyl substituted by —$(CH_2)_n$—O-lower alkyl,
cyclohexyl,
cyclohexyl substituted by $CF_3$,
cyclohexyl substituted by lower alkyl,
cyclohexyl substituted by —$(CH_2)_n$OH,
cyclohexyl substituted by —$(CH_2)_n$—O-lower alkyl,
1-bicyclo[2.2.1]hept-2-yl,
1-(7-oxa-bicyclo[2.2.1]hept-2-yl,
1-(5-exo-hydroxy-bicyclo[2.2.1]hept-2-exo-yl,
1-(5-exo-hydroxy-bicyclo[2.2.1]hept-2-endo-yl, and
1-adamantan-1-yl; and
R² is lower alkyl; and
n is 0 or 1.

7. A process for preparing a compound of formula I as defined in claim 1, which process comprises reacting a compound of formula

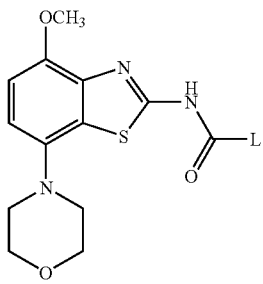

IV with a compound of formula

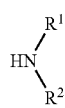

V to produce a compound of formula

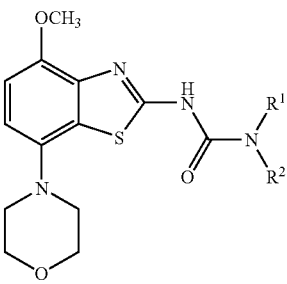

I wherein
R¹ is selected from the group consisting of
cyolopentyl,
cyclopentyl substituted by $CF_3$,
cyclopentyl substituted by lower alkyl,
cyclopentyl substituted by —$(CH_2)_n$OH,
cyclopentyl substituted by —$(CH_2)_n$—O-lower alkyl,
cyclohexyl,
cyclohexyl substituted by $CF_3$,
cyclohexyl substituted by lower alkyl,
cyclohexyl substituted by —$(CH_2)_n$OH,
cyclohexyl substituted by —$(CH_2)_n$—O-lower alkyl,
1-bicyclo[2.2.1]hept-2-yl,
1-(7-oxa-bicyclo[2.2.1]hept-2-yl,
1-(5-exo-hydroxy-bicyclo[2.2.1]hept-2-exo-yl,
1-(5-exo-hydroxy-bicyclo[2.2.1]hept-2-endo-yl, and
1-adamantan-1-yl; and
R² is lower alkyl;
n is 0 or 1; and
L is a leaving group selected from the group consisting of
such as halogen, —O-phenyl and O-lower alkyl.

8. The process of claim 6 that further comprises converting the compounds obtained into a pharmaceutically acceptable salt thereof.

9. The process of claim 7 that further comprises converting the compounds obtained into a pharmaceutically acceptable salt thereof.

10. A pharmaceutical composition which comprises a compound of formula I

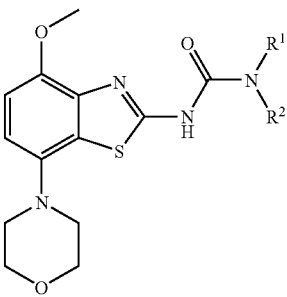

I wherein
R¹ is selected from the group consisting of
cyclopentyl,
cyclopentyl substituted by $CF_3$,
cyclopentyl substituted by lower alkyl,
cyclopentyl substituted by —$(CH_2)_n$OH,
cyclopentyl substituted by —$(CH_2)_n$—O-lower alkyl,
cyclohexyl, cyclohexyl substituted by $CF_3$,
cyclohexyl substituted by lower alkyl,
cyclohexyl substituted by —$(CH_2)_n$OH,
cyclohexyl substituted by —$(CH_2)_n$—O-lower alkyl,
1-bicyclo[2.2.1]hept-2-yl,
1-(7-oxa-bicyclo[2.2.1]hept-2-yl,
1-(5-exo-hydroxy-bicyclo[2.2.1]hept-2-exo-yl,
1-(5-exo-hydroxy-bicyclo[2.2.1]hept-2-endo-yl, and
1-adamantan-1-yl; and $R^2$ is lower alkyl; and n is 0 or 1;

or a pharmaceutically acceptable salt thereof;
and a pharmaceutically acceptable carrier.

* * * * *